US005776136A

United States Patent [19]

Sahay et al.

[11] Patent Number: 5,776,136
[45] Date of Patent: Jul. 7, 1998

[54] METHOD AND SYSTEM FOR FINISH CUTTING BONE CAVITIES

[75] Inventors: Alind Sahay, Sacramento; Zhenghao Yeh, Stevenson Ranch, both of Calif.

[73] Assignee: Integrated Surgical Systems, Inc., Sacramento, Calif.

[21] Appl. No.: 720,544

[22] Filed: Sep. 30, 1996

[51] Int. Cl.[6] .................................................. A61B 17/56
[52] U.S. Cl. ............................... 606/79; 606/80; 606/89; 623/23
[58] Field of Search ........................... 606/79, 80, 84, 606/85, 99, 89; 623/16, 23

[56] References Cited

U.S. PATENT DOCUMENTS

| 5,086,401 | 2/1992 | Glassman et al. | 395/94 |
|---|---|---|---|
| 5,198,877 | 3/1993 | Schulz | 356/375 |
| 5,383,454 | 1/1995 | Bucholz | 128/653.1 |
| 5,468,243 | 11/1995 | Halpern | 606/80 |
| 5,534,005 | 7/1996 | Tokish, Jr. et al. | 606/80 |

FOREIGN PATENT DOCUMENTS

WO 91/07726  5/1991  WIPO .......................... G06F 15/72

OTHER PUBLICATIONS

Ault, T. et al., "Frameless Patient Registration Using Ultrasonic Imaging." The Robotics Institute, School of Computer Science, Pittsburgh, Pennsylvania pp. 74–81.
Cain, P. et al., "Safety Considerations in a Surgical Robot." Integrated Surgical Systems, Inc., Sacramento, California, Paper #93–035, pp. 291–294 (1993).
Champleboux, G. et al. "An Optical Conformer for Radiotherapy Treatment Planning." *TIMC-IMAG*, Faculte de Medecine de Grenoble, La Tronche, France, pp. 69–73.
Grimson, W.E.L. et al. "Automated Registration for Enhanced Reality Visualization in Surgery." pp. 82–89.
Kazanzides, P. et al. "Architecture of a Surgical Robot." IEEE Conference on Systems, Man, and Cybernetics, Chicago, Illinois, pp. 1624–1629 (1992).

Kazanzides, P. et al. "Force Sensing and Control for a Surgical Robot." IEEE Conference on Robotics and Automation, Nice, France, pp. 612–617 (May, 1992).
Kazanzides, P. et al. "Surgical and Industrial Robots: Comparison and Case Study." Integrated Surgical Systems, Inc., Sacramento, California, pp. Oct. 19 –Oct. 26 (circa 1994).
Lavalle, S. et al. "Computer Assisted Spine Surgery: A Technique for Accurate Transpedicular Screw Fixation Using CT Data and a 3–D Optical Localizer." *TIMC* Faculte de Medecine de Grenoble, La Tronche, France, pp. 315–322 (1995).
Lea, J.T. et al. "Registration and Immobilization for Robot–Assisted Orthopaedic Surgery." Department of Mechanical Engineering, Northwestern University, Evanston, Illinois, pp. 63–68.
Lombardi, Adolph V., Jr. "Cement Removal in Revision Total Hip Arthroplasty." *Seminars in Arthroplasty* 3(4) :264–272 (Oct., 1992).
Mittelstadt, B. et al. "Development of a Surgical Robot for Cementless Total Hip Replacement." *Robotics* 3:553–560 (1993).
Mittelstadt, B. et al. "Robotic Surgery: Achieving Predictable Results in an Unpredictable Environment." Integrated Surgical Systems, Inc., Sacramento, California, pp. 367–372 (1993).

(List continued on next page.)

*Primary Examiner*—Michael Buiz
*Assistant Examiner*—David O. Reip
*Attorney, Agent, or Firm*—Townsend and Townsend and Crew LLP

[57] ABSTRACT

Methods and systems for finish cutting of bone cavities rely on making a plurality of axial finish cuts along the cavity wall. Finish cuts are made using a rotary cutter, and a sufficient number of cuts are made to limit the radial height of cusps between adjacent cuts resulting from the arcuate shape of the cut profile. Cutting time is reduced by selectively terminating the axial lengths of the finish cuts in a manner which does not result in unacceptably high radial cusp heights between adjacent cuts.

9 Claims, 7 Drawing Sheets

OTHER PUBLICATIONS

Mittelstadt, B. et al. "The Evolution of a Surgical Robot from Prototype to Human Clinical Use," Integrated Surgical Systems, Inc., Sacramento, California, pp. 36–41 (1994).

Nolte, L. et al. "A Novel Approach to Computer Assisted Spine Surgery," M.E. Muller Institute for Biomechanics, University of Bern, Bern, Switzerland, pp. 323–328 (1995).

Paul, H. et al. "Development of a Surgical Robot for Cementless Total Hip Arthroplasty," *Clinical Orthopaedics* 285:57–66 (1992).

Peria, O. et al. "Accurate Registration of SPECT and MR Brain Images of Patients Suffering from Epilepsy and Calibration," *TIMB–TIMC–IMAG* Faculte de Medecine de Grenoble, La Tronche, France, pp. 58–62.

Potamianos, P. et al. "Intra–Operative Imaging Guidance for Keyhole Surgery Methodology and Calibration," Robotics Group, Imperial College of Science, Technology and Medicine, London, United Kingdom, pp. 98–104.

Simon, D. et al. "Techniques for Fast and Accurate Intra–Surgical Registration," Robotics Institute, Carnegie Mellon University, Pittsburgh, Pennsylvania, pp. 90–97.

METHOD AND SYSTEM FOR FINISH CUTTING BONE CAVITIES

BACKGROUND OF THE INVENTION

CROSS-REFERENCE TO RELATED APPLICATIONS

The disclosure of the present patent application is related to copending U.S. patent application Ser. No. 08/526,826, filed on Sep. 11, 1995, and to U.S. patent application Ser. No. 08/606,989, filed on Feb. 22, 1996, the full disclosures of which are incorporated herein by reference. The disclosure of the present application is further related to application serial no. 08/ (Attorney Docket No. 17150-000300US), filed on the same date as the present application, the full disclosure of which is incorporated herein by reference.

1. Field of the Invention

The present invention relates generally to surgical methods and systems. More particularly, the present invention relates to a method and system for finish cutting of a bone cavity for receiving a femoral prosthesis in total hip replacement surgery.

Total hip replacement (THR) surgery (also called primary total hip arthroplasty) is a surgical procedure where a surgeon replaces a patient's ball-and-socket joint with a prosthetic device. The prosthetic device includes an acetabular cup and a femoral prosthesis. The femoral prosthesis provides the replacement "ball" and the acetabular cup provides the replacement "socket" of the ball-and-socket joint. Thousands of people today are able to retain mobility and have reduced pain because of total hip replacement surgery.

FIG. 1 shows the anatomical positions of the prostheses which are implanted by total hip replacement surgery prostheses. A pelvis 12 is implanted with an acetabular cup 14. The corresponding femur 16 is implanted with a femoral prosthesis 18. The femoral prosthesis 18 includes a head 20 and a stem 22. The surgeon implants the femoral prosthesis 18 by first removing the femoral head from the bone and then excavating to and extending the femoral canal 24 within the femur so that the femoral stem 22 of the prosthesis 18 may be placed in the excavated femoral canal adjacent to the cortical bone 26. Once the femoral prosthesis 18 is implanted, the femoral head 20 of the prosthesis is disposed adjacent to the trabecular bone 28.

Surgeons typically prepare a cavity for the femoral stem with inaccurate methods. Reamers (hand-held drills) and broaches (serrated cutting tools) are utilized by surgeons to produce the femoral cavity. Laboratory tests have shown that the cavities produced by these methods are irregular, resulting in relatively large gaps between the bone and the prosthesis. These gaps may result when the broach tears out chunks of trabecular bone instead of making a precise cut. Additionally, the gaps may be caused by the tendency of a broach to cut the material with the least resistance when it makes contact with dense trabecular or cortical bone. Bone cement (polymethylmethacrylate or PMMA) is typically utilized to fill in the gaps between the femur and the femoral prosthesis.

Recently, innovative systems have been developed for performing robot-assisted total hip replacement surgery. The ORTHODOC™ presurgical planning workstation developed by Integrated Surgical Systems, Inc., Sacramento, Calif., assignee of the present application, allows the surgeon to plan the placement of the femoral prosthesis on a workstation utilizing an image of the femur, typically a computerized tomography (CT) scan image, and an image of the prosthesis. Once placement of the prosthesis has been planned, the workstation generates data defining a cavity model for use by a computer-controlled robotic system intended to cut the cavity which receives the femoral prosthesis, such as the ROBODOC™ surgical robot system which was also developed by Integrated Surgical Systems.

Of particular interest to the present invention, the data generated for the robot include "cut files" which comprise detailed instructions for the manipulation of a robot arm that carries a rotary cutter, such as a disk cutter or a ball cutter. The cutting instructions include a plan for "rough cutting" the interior of the bone to remove a major portion of the bone material and to produce a "rough" cavity having walls which approximate the desired final dimensions of the cavity envelope. Such rough cutting can be achieved, for example, by axially penetrating a rotary cutter into the bone and then translating the cutter around a peripheral section of the desired bone cavity envelope. After cutting a first peripheral section, the cutter is further penetrated into the bone and again translated around a peripheral section of the cavity. Since the cavity is tapered in the direction from the entrance to the distal terminus, each successive peripheral section will be smaller than the prior section. This results in a "stepped" profile on the cavity wall which must be smoothed out in a subsequent finish cutting phase.

Finish cutting is performed in order to smooth the cavity wall to within acceptable tolerances, typically +/0.1 mm. Finish cutting is performed by axial translation of the rotary cutter along a plurality of predefined "finish cut paths" which follow the wall of the cavity model. As described below, a large number of such axial finish cuts are required in order to provide a wall smoothness within the desired tolerance. Often, as many as 20 to 50 axial cuts are needed.

The use of rotary cutters places certain limitations on the finish cutting protocol. It will be appreciated that a rotary cutter creates in the cavity wall a groove or channel having an arcuate cross-section, as shown in FIGS. 1A–1C. A cross-section of bone B as shown with the planned cavity envelope 30 in broken line and a rough cut cavity wall 32. It is desired to finish cut the cavity so that the wall is moved radially outward to lie proximate the planned envelope 30. To do so, a rotary cutter (not shown) is translated axially (i.e. in a direction normal to the cross-sectional view) to generate an arcuate groove 34, as shown in FIG. 1A. In particular, the center point of the cutter is passed along a cut path (CP #1) which is spaced radially inward from the defined cavity wall 30 by a distance equal to the radius of the cutter. The intent is to have an outer most tangential point 36 axially follow the envelope 30 for the entire length of the cavity.

After the first cut path (CP #1) is completed, the cutter will be moved to cut along a second path (CP #2), as shown in FIG. 1B, to form a second arcuate channel 38. Typically this will be done from the distal end of the cavity by translating the cutter toward the entrance end so that cut path CP #2 can be formed with minimal movement of the robot arm. The cutting pattern is continued until the cavity is finish cut around its entire periphery. Such finish cutting using axial passes of a rotary cutter, however, results in an uneven "scalloped" profile, as shown in more detail in FIG. 1C. In particular, a cusp 40 is left between adjacent finish cuts 34 and 38, where the cusp has a height (h) which is determined by the distance (d) between cut paths CP #1 and CP #2. By placing the cut paths circumferentially closer together, i.e. by reducing distance d, the cusp height h can be reduced to below any specified tolerance. Typical cusp height tolerances are in the range from +/−0.05 mm, requiring a distance d in the range from 1.4 to 1.6 for cutters having a radius from 5.0 to 6.5.

Thus, it can be seen that a large number of axial finish cuts must be performed to achieve an acceptable wall smoothness in the cutting procedures described above. The need to perform such a large number of axial finish cuts is time-consuming and significantly lengthens the time necessary to perform robotic total hip replacement surgery. It would therefore be desirable to provide improved methods and systems for cutting bone cavities using rotary cutters which could achieve an acceptable smoothness in less time than is presently required. It would further be desirable if such improved methods and systems could be implemented with minimum changes in the existing robotic methods and systems which have been described above. The present invention meets at least some of the above objectives.

2. Description of the Background Art

Conventional techniques for bone cement removal in revision total hip replacement surgery are described in (1) Lombardi, Jr., A.: "Cement Removal in Revision Total Hip Arthroplasty," *Seminars in Arthroplasty*, Volume 3, No. 4, Pages 264–272, October 1992.

The ORTHODOC™ presurgical planning workstation and the ROBODOC™ robotic surgical system are described in a number of references, including the following: (2) Kazanzides, P., Zuhars, J., Mittelstadt, B. D., Taylor, R. H.: "Force Sensing and Control for a Surgical Robot," *Proc. IEEE Conference on Robotics & Automation*, Pages 612–616, Nice, France, May 1992. (3) Kazanzides, P., Zuhars, J., Mittelstadt, B. D., Williamson, B., Cain, P., Smith, F., Rose, L., Mustis, B.: "Architecture of a Surgical Robot," *Proc. IEEE Conference on Systems, Man, and Cybernetics*, Chicago, Ill., Pages 1624–1629, October, 1992. (4) Paul, H. A., Bargar, W. L., Mittelstadt, B., Musits, B., Taylor, R. H., Kazanzides, P., Zuhars, J., Williamson, B., Hanson, W.: "Development of a Surgical Robot For Cementless Total Hip Arthroplasty," *Clinical Orthopaedics*, Volume 285, Pages 57–66, December 1992. (5) Kazanzides, P., Mittelstadt, B. D., Zuhars, J., Cain, P., Paul, H. A., "Surgical and Industrial Robots: Comparison and Case Study," *Proc. International Robots and Vision Automation Conference*, Pages 1019–1026, Detroit, Mich., April 1993. (6) Mittelstadt, B., Kazanzides, P., Zuhars, J., Williamson, B., Pettit, R., Cain, P., Kloth, D., Rose, L., Musits, B.: "Development of a surgical robot for cementless total hip replacement," *Robotica*, Volume 11, Pages 553–560, 1993. (7) Mittelstadt B., Kazanzides, P., Zuhars, J., Cain, P., Williamson, B.: "Robotic surgery: Achieving predictable results in an unpredictable environment," *Proc. Sixth International Conference on Advanced Robotics*, Pages 367–372, Tokyo, November, 1993. (8) Cain, P., Kazanzides, P., Zuhars, J., Mittelstadt, B., Paul, H.: "Safety Considerations in a Surgical Robot," *Biomedical Sciences Instrumentation*, Volume 29, Pages 291–294, San Antonio, Tex., April 1993. (9) Mittelstadt, B. D., Kazanzides, P., Zuhars, J., Williamson, B., Cain, P., Smith, F. Bargar, W.: "The Evolution of A Surgical Robot From Prototype to Human Clinical Use," in *Proc. First International Symposium on Medical Robotics and Computer Assisted Surgery*, Volume I, Pages 36–41, Pittsburgh, Pa., September 1994.

Other publications which describe image registration in robotic surgical and other procedures include the following: (10) Grimson, W. E. L., Lozano-Perez, T., Wells III, W. M., Ettinger, G. J., White, S. J., Kikinis, R.: "Automated Registration for Enhanced Reality Visualization in Surgery," *Proceedings of the First International Symposium on Medical Robotics and Computer Assisted Surgery*, Volume I, Sessions I–III, Pages 82–89, Pittsburgh, Pa., Sep. 22–24, 1995. (11) Nolte, L. P., Zamorano, L. J., Jiang, Z., Wang, Q., Langlotz, F., Arm, E., Visarius, H.: "A Novel Approach to Computer Assisted Spine Surgery," *Proceedings of the First International Symposium on Medical Robotics and Computer Assisted Surgery*, Volume II, Session IV, Pages 323–328, Pittsburgh, Pa., Sep. 22–24, 1994. (12) Lavallée, S., Sautot, P., Troccaz, J., Cinquin, P., Merloz, P.: "Computer Assisted Spine Surgery: a technique for accurate transpedicular screw fixation using CT data and a 3-D optical localizer," *Proceedings of the First International Symposium on Medical Robotics and Computer Assisted Surgery*, Volume II, Session IV, Pages 315–321, Pittsburgh, Pa., Sep. 22–24, 1994. (13) Potamianos, P., Davies, B. L., Hibberd, R. D.: "Intra-Operative Imaging Guidance For Keyhole Surgery Methodology and Calibration," *Proceedings of the First International Symposium on Medical Robotics and Computer Assisted Surgery*, Volume I, Sessions I–III, Pages 98–104, Pittsburgh, Pa., Sep. 22–24, 1994. (14) Simon, D. A., Hebert, M., Kanade, T.: "Techniques for Fast and Accurate Intra-Surgical Registration," *Proceedings of the First International Symposium on Medical Robotics and Computer Assisted Surgery*, Volume I, Sessions I–III, Pages 90–97, Pittsburgh, Pa., Sep. 22–24, 1995. (15) Péria, O., Francois-Joubert, A., Lavallée, S., Champleboux, G., Cinquin, P., Grand, S.: "Accurate Registration of SPECT and MR brain images of patients suffering from epilepsy or tumor," *Proceedings of the First International Symposium on Medical Robotics and Computer Assisted Surgery*, Volume II, Session IV, Pages 58–62, Pittsburgh, Pa., Sep. 22–24, 1995. (16) Lea, J. T., Watkins, D., Mills, A., Peshkin, M. A., Kienzle III, T. C., Stulberg, D. S.: "Registration and Immobilization for Robot-Assisted Orthopaedic Surgery," *Proceedings of the First International Symposium on Medical Robotics and Computer Assisted Surgery*, Volume I, Sessions I–III, Pages 63–68, Pittsburgh, Pa., Sep. 22–24, 1995. (17) Ault, T., Siegel, M. W.: "Frameless Patient Registration Using Ultrasonic Imaging," *Proceedings of the First International Symposium on Medical Robotics and Computer Assisted Surgery*, Volume I, Sessions I–III, Pages 74–81, Pittsburgh, Pa., Sep. 22–24, 1995. (18) Champleboux, G., Lavallée, S., Cinquin, P.: "An Optical Conformer for Radiotherapy Treatment Planning," *Proceedings of the First International Symposium on Medical Robotics and Computer Assisted Surgery*, Volume I, Sessions I–III, Pages 69–73, Pittsburgh, Pa., Sep. 22–24, 1995.

A system and method for performing robotically assisted surgery is described in U.S. Pat. No. 5,086,401. Computer-assisted imaging and probe tracking systems are described in U.S. Pat. No. 5,383,454; U.S. Pat. No. 5,198,877; and WO 91/07726.

SUMMARY OF THE INVENTION

The present invention provides improved methods and systems for cutting tapered cavities into elongate (long) bones, such as cavities intended to receive implants in femurs as part of total hip replacement surgery. Such cavities will have an enlarged entrance dimension which tapers down in an axial direction to a terminal end having a smaller cross-sectional area. The method is performed in two steps, with the bone first being rough cut to produce a rough cavity and then being finish cut by translating a rotary cutter axially along a plurality of circumferentially spaced-apart finish cut paths. Such finish cuts produce axially oriented grooves or channels in the bone cavity wall, where the grooves have arcuate cross-sectional profiles and are separated by axially oriented "cusps" which are peaks between the grooves resulting from the accurate groove profiles. The improvement herein comprises selectively shortening the axial lengths of some but not all of the finish cut paths to a distance less than the axial cavity length in order to reduce the total cutting time of the procedure.

In preferred aspects of the present invention, the finish cut paths will usually be equally spaced-apart, i.e. defined center lines for the rotary cutter which are separated by equal distances at the cavity entrance. The circumferential distances between the finish cut paths will diminish uniformly as the cavity tapers toward the terminal end thereof, and the improvement further comprises terminating an axial finish path when the distance between the two immediately adjacent finish cut paths becomes equal to or less than the distance between the finish cut paths at the entrance end of the cavity. By assuring that the adjacent finish cut paths have become at least as close as the originally adjacent cut paths, the "third" cut path therebetween becomes unnecessary to maintain the cusp therebetween below a minimum radial cusp height and can be eliminated.

A more specific method according to the present invention for cutting a tapered cavity into an elongate bone comprises providing a cavity model defining a cavity envelope having dimensions including axial cavity length from an entrance end to a terminal end of the cavity as well as cross-sectional geometries and dimensions at various depths within the cavity from the entrance toward the terminal end. The cavity is rough cut to remove bone material along the cavity axis, i.e. in the depth direction, to approximate the shape of the envelope of the cavity model. The tapered cavity is then finish cut using a rotary cutter having a radius (r) using the following protocol. A plurality of finish cut paths are defined along lines which are spaced radially inward from the cavity envelope by a distance equal to the radius r. The cut paths are circumferentially spaced-apart at the entrance end by a distance (d) selected to produce a radial cusp height between adjacent cuts at or below a maximum value. For the reasons described above, it will be appreciated that the radial cusp height between any two cut paths will diminish as the cavity cross-sectional size tapers and the finish cut paths move circumferentially closer to each other. The finish cuts are then made using the rotary cutter along each of the finish cut paths, but the axial length along any particular cut path is terminated when the two cut paths immediately adjacent to the particular cut path, i.e. when the two cut paths lying on either side of the particular cut path become sufficiently close so that the cusp height between the two adjacent cut paths is equal to or less than the preselected radial cusp height value. Cutting along the two adjacent cut paths will be continued while cutting along the preselected cut path which lies between said adjacent cut paths will be terminated.

The method just described will generally employ a rough cutting protocol which is the same as that employed in the prior art as described above. Both the rough cutting step and the finish cutting step will usually, but not necessarily, employ the same rotary cutter, which may be a disk cutter or a ball cutter, or any other conventional rotary cutter.

Preferably, the finish cut paths are defined by first determining the number ($n_0$) of finish cut paths necessary to produce the predetermined cusp height when the cut paths are evenly distributed around the cavity circumference at the cavity entrance. The circumferential length ($L_0$) about the cavity envelope at the entrance end is also determined, and the depth at which a particular cut path can be terminated may then be calculated as follows. The circumferential length (L) about the cavity is determined at increasingly greater depths until a circumferential length $L_1$ having a diminished value equal to $L_0/2$ is found. At that point, alternate ones of the finish cut paths may be terminated since the adjacent cut paths have moved sufficiently close to one another so that the resulting cusp height is at or below the maximum acceptable cusp height. It will be appreciated, of course, that two immediately adjacent finish cut paths can never be simultaneously eliminated. Thus, if there is an even number of cut paths, alternate cut paths may be terminated. If there is an odd number of cut paths, alternate cut paths except for one may be terminated.

As described above, the total number of finish cut paths is reduced by approximately one-half at a cavity depth wherein the circumferential length of the cavity has been reduced by one-half from the initial length at the cavity entrance. Subsequent reductions in the number of cutting paths may be implemented every time the circumferential length (L) of the cavity is reduced by an additional one-half i.e. at depths where the circumferential length reaches $L_0/4$, $L_0/8$, $L_0/16$, etc. At some point, of course, the end of the cavity will be reached and it will no longer be possible or necessary to further reduce the number of finish cut paths.

The present invention still further provides a method for generating cutting instructions for a computer-controlled robotic surgical cutting system employing a rotary cutter having a radius (r), usually of the type intended for cutting a femur or other elongate bone prior to receiving an implant. The method for generating cutting instructions comprises receiving a cavity model defining a cavity envelope to be cut into the bone, where the cavity is tapered along an axis from an entrance end of the cavity to a small terminal end of the cavity. According to the method, a plurality of finish cut paths are generated which are spaced radially inward from the envelope by a distance equal to r and which are circumferentially spaced-apart by a distance (d) selected to produce at the entrance end of the cavity a preselected cusp pipe between adjacent cuts. As described above, the cusp height will diminish as the cavity cross-sectional area is reduced and the finish cuts move circumferentially closer together. The cutting instructions further rely on determining axial termination locations for each of the finish cut paths, where a particular cut path is terminated when the two cut paths immediately adjacent to said particular path becomes sufficiently circumferentially close so that the cusp pipe between the two adjacent cut paths is equal to or less than the preselected radial cusp pipe. Particular numerical techniques for implementing such determining steps are described above.

The present invention still further provides a computer program product for use with a computer readable code defining a bone cavity model including a cavity envelope to be cut. The cavity model is tapered along an axis from an entrance end to a smaller terminal end, and the computer program comprises computer readable code for generating a plurality of finish cut paths, generally as described above. The computer program further comprises computer readable code for determining axial termination locations, also as generally described above. The computer readable code will be incorporated into a tangible medium for storing the code, such as a magnetic disk, tape, CD ROM, flash or other computer memory, or other conventional articles.

DESCRIPTION OF THE SPECIFIC EMBODIMENTS

The present invention provides methods, systems, and apparatus for assisting in the robotically implemented cutting of cavities into elongate (long) bones, such as the femur, in surgical procedures, such as hip replacement surgery, long bone osteotomies, and the like. In particular, the methods, systems, and apparatus are useful for controlling a rotary cutter being manipulated by a surgical robot to "finish cut" a bone cavity to smooth the walls to within an acceptable tolerance, e.g. +/−0.05 mm. The methods, system, and apparatus specifically provide for controlling axial translation of the rotary cutter along a plurality of predefined finish cut paths, where the rotary cutters result in a plurality of generally parallel axial grooves having arcuate cross-sections in the wall. The present invention specifically provides for maintaining the "radial cusp height" between such parallel axial grooves to within the desired tolerance while minimizing the number and length of such axial grooves which must be formed during the procedure. Details of the methods, systems, and apparatus for achieving such improved methods are described in detail below.

Figure 2:
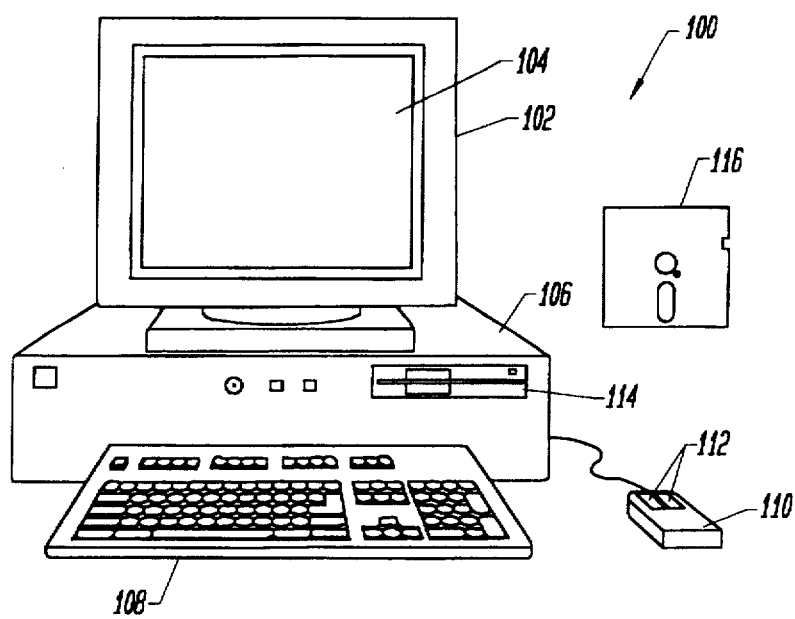
FIG. 2 illustrates an exemplary computer system capable of implementing the method and executing the software of the present invention.

FIG. 2 illustrates an example of a computer system capable of executing software embodying the methods of the present invention. FIG. 2 shows a computer system 100 which includes a monitor 102, display screen 104, cabinet 106, keyboard 108, and mouse 110. Mouse 110 may have one or more buttons such as mouse buttons 112. Cabinet 106 houses a floppy drive 114 or a hard drive (not shown) which may be utilized to store and retrieve the computer readable code of software programs incorporating the present invention, patient information, image data of bones, files defining cutting contours, and the like. Although a floppy diskette 116 is shown as the removable media, other removable tangible media including CD-ROM, tape, and flash memory may be utilized. Cabinet 106 also houses familiar computer components (not shown) such as a processor, memory, and the like.

Figure 3:
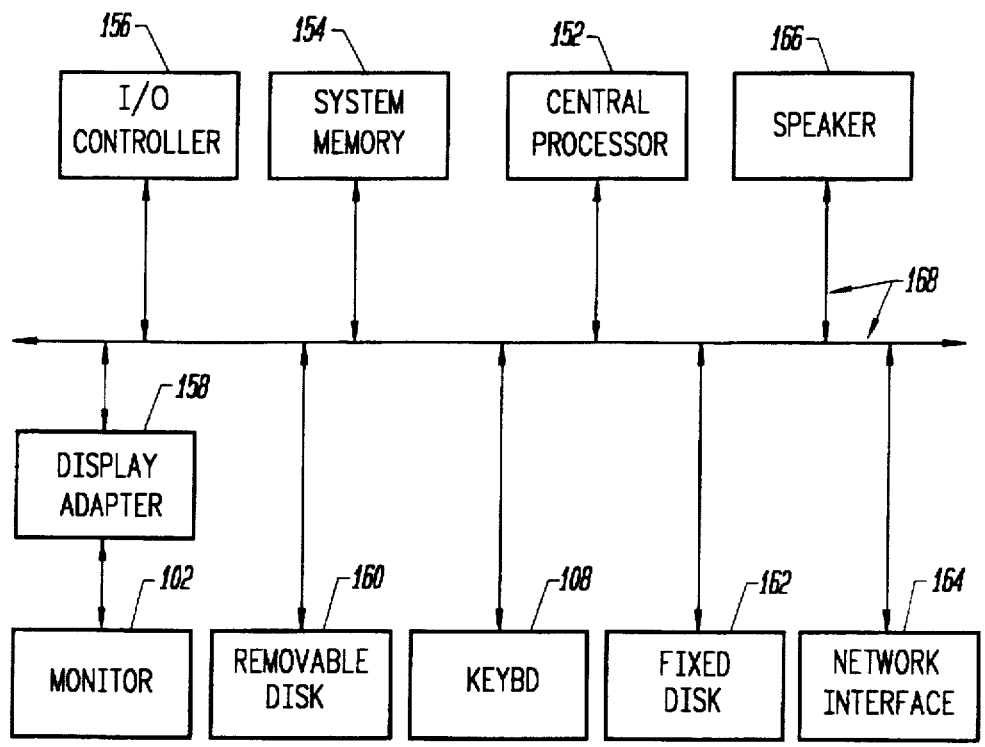
FIG. 3 illustrates a system block diagram typical of the computer system of FIG. 2.

FIG. 3 shows a system block diagram of computer system 100. As in FIG. 2, computer system 100 includes monitor 102 and keyboard 108. Computer system 100 further includes subsystems such as a central processor 152, system memory 154, I/O controller 156, display adapter 158, removable disk 160, fixed disk 162, network interface 164, and speaker 166. Other computer systems suitable for use with the present invention may include additional or fewer subsystems. For example, another computer system could include more than one processor 102 (i.e., a multi-processor system) or a cache memory.

Arrows such as 168 represent the system bus architecture of computer system 100. However, these arrows are illustrative of any interconnection scheme serving to link the subsystems. For example, a local bus could be utilized to connect the central processor to the system memory and display adapter. Computer system 100 shown in FIG. 3 is but an example of a computer system suitable for use with the present invention. Other configurations of subsystems suitable for use with the present invention will be readily apparent to one of ordinary skill in the art.

In a preferred embodiment, the present invention operates on an IBM RS/6000 computer running the UNIX operating system. However, the invention is not limited to any computer architecture or operating system and the description of the embodiments that follows is for purposes of illustration and not limitation.

Figure 4:
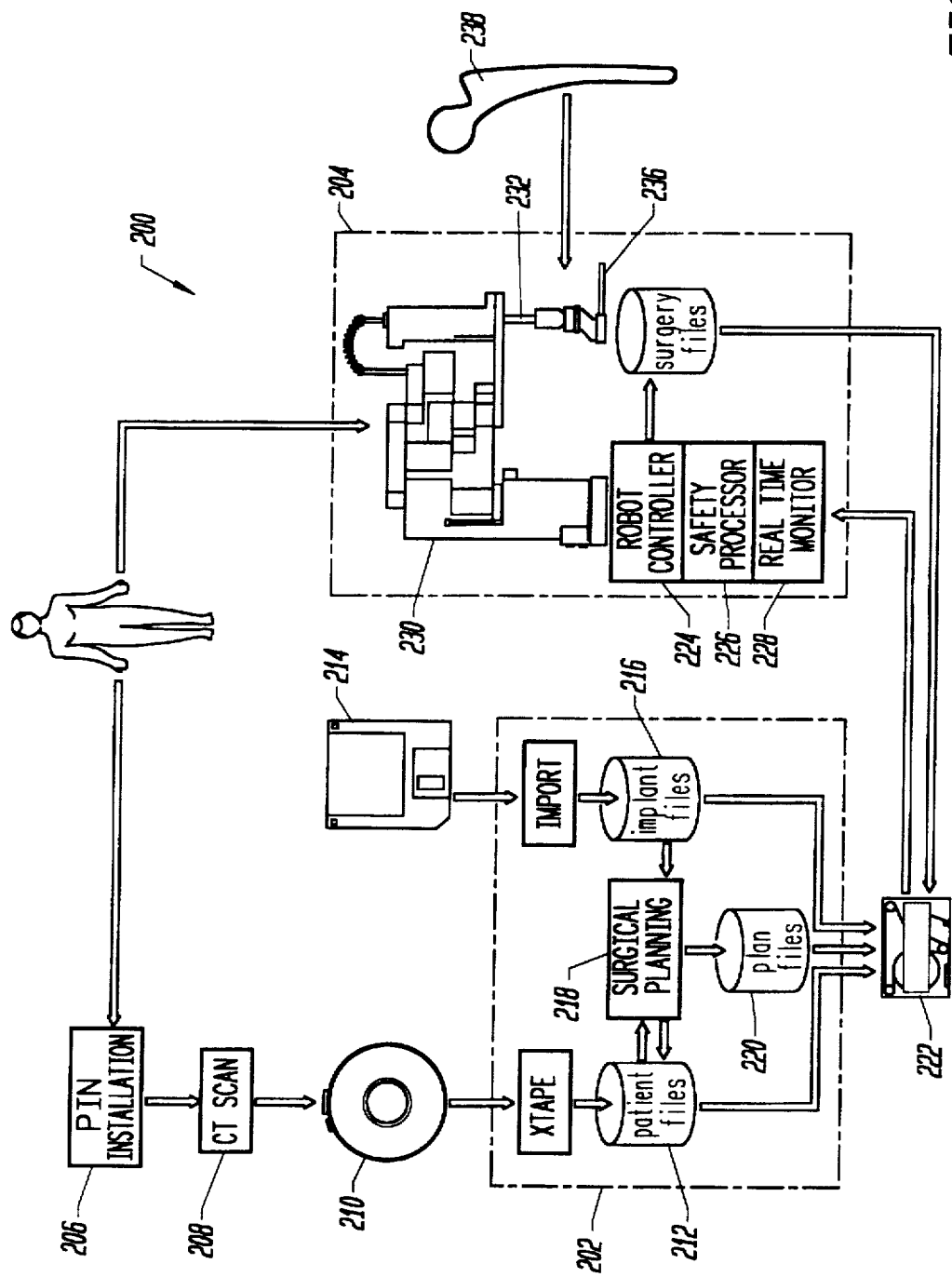
FIG. 4 illustrates the architecture of a surgical planning system and robotic operative system capable of implementing the methods and executing the software of the present invention.

FIG. 4 illustrates an architecture of a robotic surgical system including a presurgical planning component and a surgical component which are capable of implementing the methods of the present invention. A system 200 for total hip replacement surgery may include both a presurgical planning workstation 202 and a surgical robot system 204. In a preferred embodiment, the presurgical planning workstation is the ORTHODOC™ presurgical planning workstation which includes an IBM RS/6000 computer. In a preferred embodiment, the surgical robot system is the ROBODOC™ surgical robot system. The following will describe the present invention in reference to a preferred embodiment utilizing the ORTHODOC™ presurgical planning workstation and the ROBODOC™ surgical robot system. However, other systems may be utilized and therefore this description is for purposes of illustration and not limitation.

For alignment of the femur, the surgical robot typically system relies on the surgical implantation of a pair of metallic pins on the distal (lower) end of the femur and one additional metallic pin in the proximal end of the bone. These pins are readily apparent in the CT image of the bone and can thus be relied on to register the bone image with the robotic coordinate space by engaging a probe placed on the manipulator arm against each of the pins. Accordingly, prior to surgery, pin installation 206 will be performed followed by a CT scan 208. An alternate pinless registration method and system is described in copending application Ser. No. 08/526,826, the disclosure of which has previously been incorporated herein by reference. The image data from the CT scan is stored on a magnetic tape 210. Presurgical planning workstation 202 reads the CT scan data and stores it in a database of patient files 212. Although the present invention will be described as utilizing a CT scan, other imaging techniques may be utilized including x-rays.

Implant designs of different femoral prostheses may be stored on a floppy disk 214. The implant designs are typically in the form of computer aided design (CAD) models which may be available from the manufacturers. The implant designs are read and converted into a database of implant files 216. The presurgical planning workstation utilizes data from the patient files and implant files to allow a surgeon to perform surgical planning 218 of the revision total hip replacement. Details of the surgical planning will be described in more detail below. Surgical planning generates plan files 220 which may include a cut binary file and a check volume file. The plan files may be placed on a digital tape 222 for use by the surgical robot system.

Surgical robot system 204 includes a robotic controller 224 (typically a digital processor in the form of a programmable computer), a safety processor 226, a real time monitor computer 228, and a robot 230. The robot can be any conventional industrial robot having a manipulatable arm 232 preferably having at least 5 axes and capable of high precision placement. A suitable robotic is available from Sankyo Robotics with the model designation SR-5427-ISS. For use in the present invention, a force sensor 234 is mounted at the distal end of arm 232, and an effector in the form of a probe 236 or a surgical cutting tool (not shown) may be attached to the force sensor to cut a cavity for a femoral prosthesis 238.

The surgical robot system further includes a display monitor and a bone motion monitor (both not shown). The force sensor, safety processor, real time monitor, and bone motion monitor, each help monitor the position, slippage, and blockage of the effector end of the manipulatable arm 232 while the femur is held in place in a fixator assembly (not shown). Real time monitoring of these parameters helps assure that the robotic system is operating as planned. Details of these monitoring systems are described in the literature cited above which describes the ROBODOC™ robotic surgical system.

Figure 5:
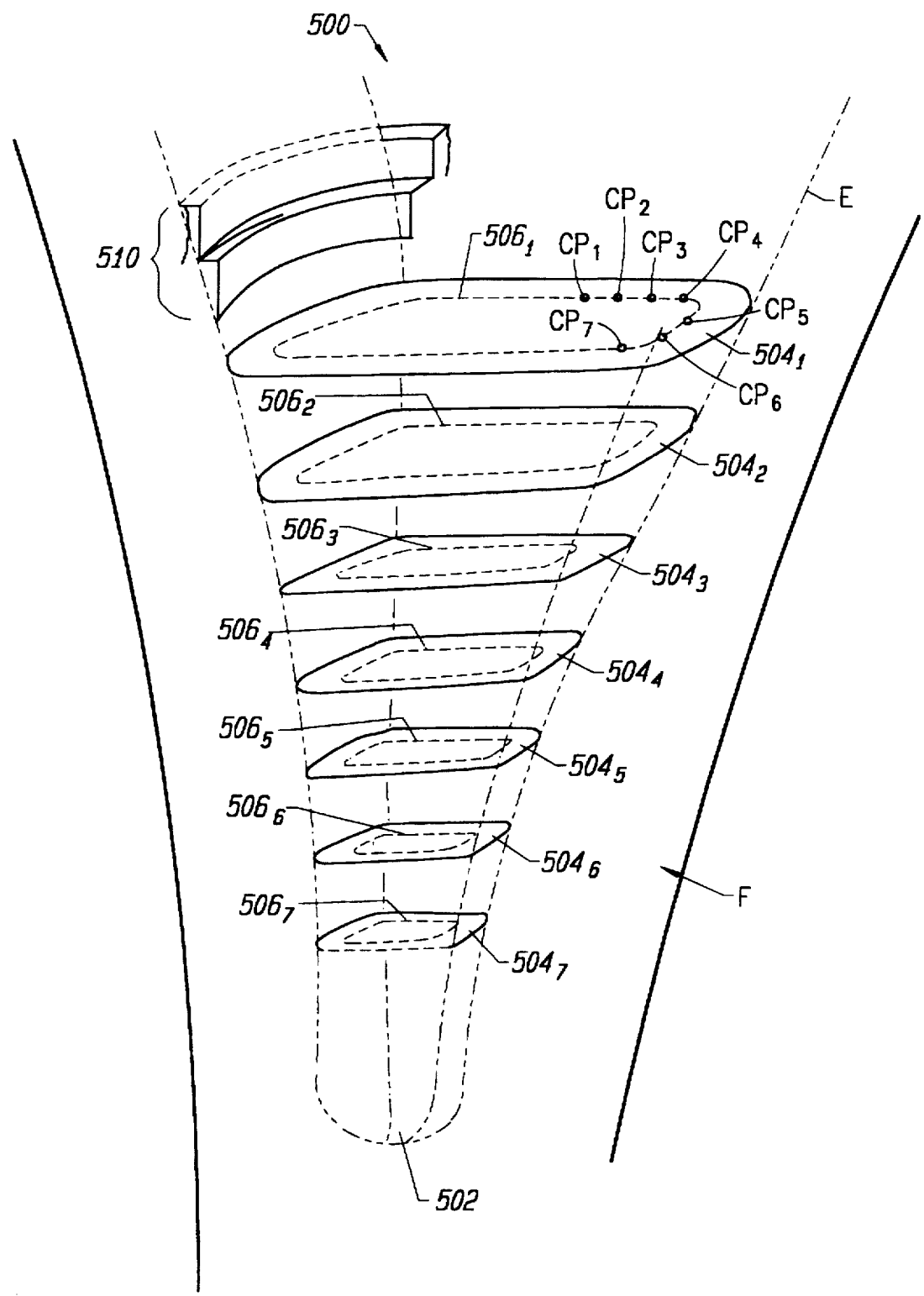
FIG. 5 is a schematic illustration of a tapered bone cavity formed in a femur or other elongate bone with a plurality of axially spaced-apart cross-sectional templates shown therein.

Referring now to FIG. 5, a femur F is illustrated schematically with a cavity envelope E shown therein. The cavity envelope E is available in the presurgical planning system and has an enlarged entrance end 500 and a terminal end 502, with the cross-sectional area of the cavity generally diminishing in the direction from the entrance end to the terminal end. A plurality of cross-sectional templates $504_i$ are shown within the periphery of the envelope E, with each template having a broken line $506_i$ indicating a line radially inset from the perimeter or circumference of the template $504_i$ by a distance r equal to the radius of the rotary cutter used to perform the finish cutting operation of the present invention.

Prior to finish cutting, however, it will be necessary to rough cut the bone F to remove a major portion of the bone material lying within E in any conventional manner. Conveniently, the method employed by the ROBODOC™ surgical system described above for rough cutting may be employed. That is, a rotary cutter, such as a disk cutter or a ball cutter may be manipulated by the surgical robot so that the cutter penetrates axially to within the cavity defined by envelope E. The cutter is then moved transversely so that it approaches the periphery of the envelope E and is thereafter translated in a desired pattern to remove a transverse layer of material, usually leaving a generally axial wall around the material that has been removed. The resulting step-shaped profile left on the cavity wall is schematically shown in region 510 of FIG. 5. Other rough cutting techniques could be developed, and such initial rough cutting procedure does not form a novel aspect of the present invention.

Figure 1:
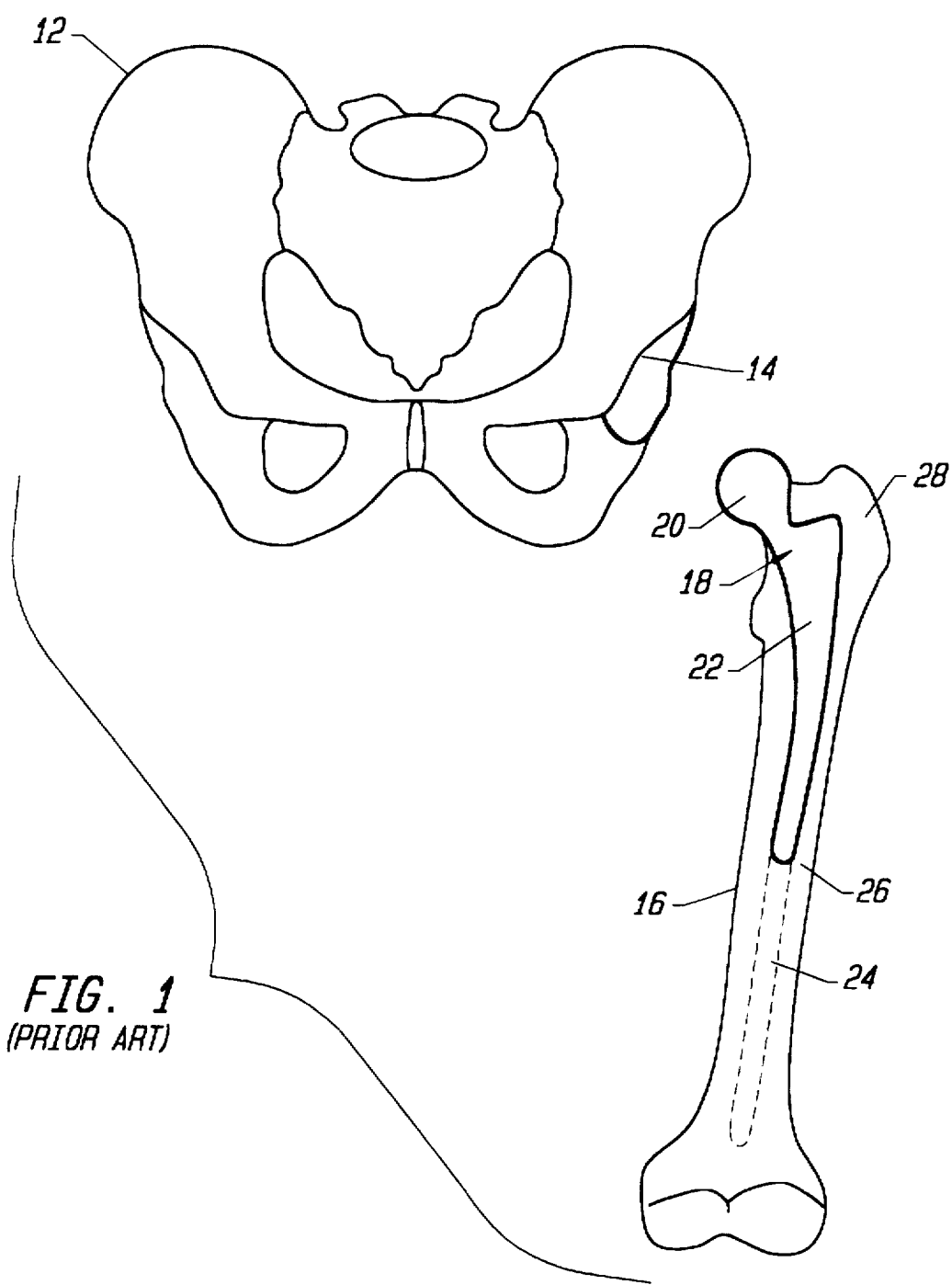
FIG. 1 illustrates the placement of both the femoral prosthesis and acetabular cup as implanted after total hip replacement surgery.
Figure 1A:
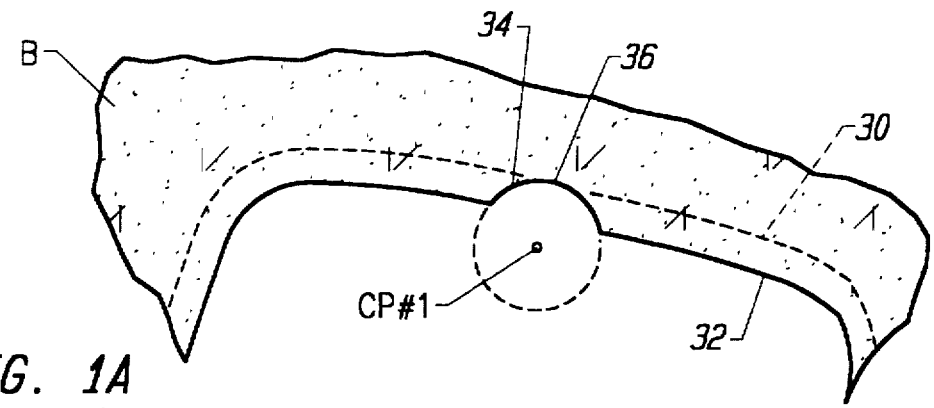
FIGS. 1A–1C illustrate the channel profiles left in the wall of a bone cavity after finish cutting using a rotary cutter.
Figure 1B:
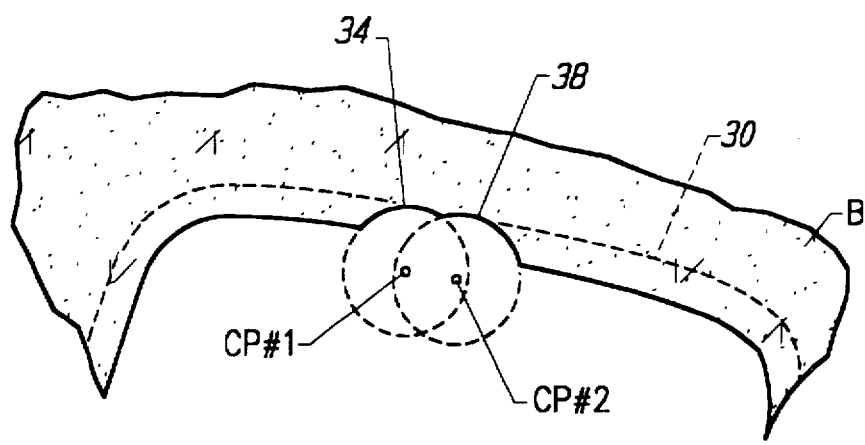
Figure 1C:
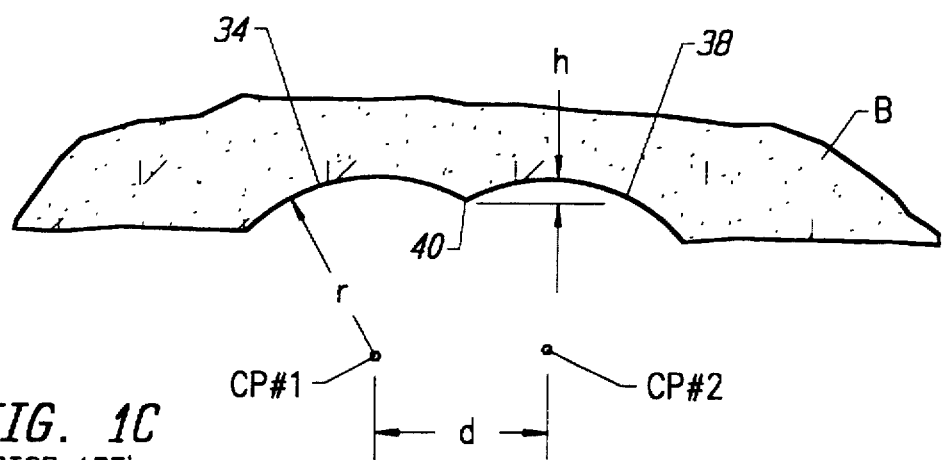

Once the cavity bounded by envelope E has been initially cut so that its peripheral wall approximates the envelope E (and typically having the stepped-shape profile shown in region 510), it is necessary to finish cut along the walls of the cavity in order to smooth the walls to a desired degree. The present invention will achieve such smoothing using a rotary cutter manipulated by the surgical robot to form a plurality of generally axial cut paths along the wall. The method will generally be as described previously in connection with FIGS. 1A–1C, except that the lengths of individual finish cut paths will be adjusted to reduce the total cut time required for finish cutting the cavity, as will now be described in detail.

Figure 6:
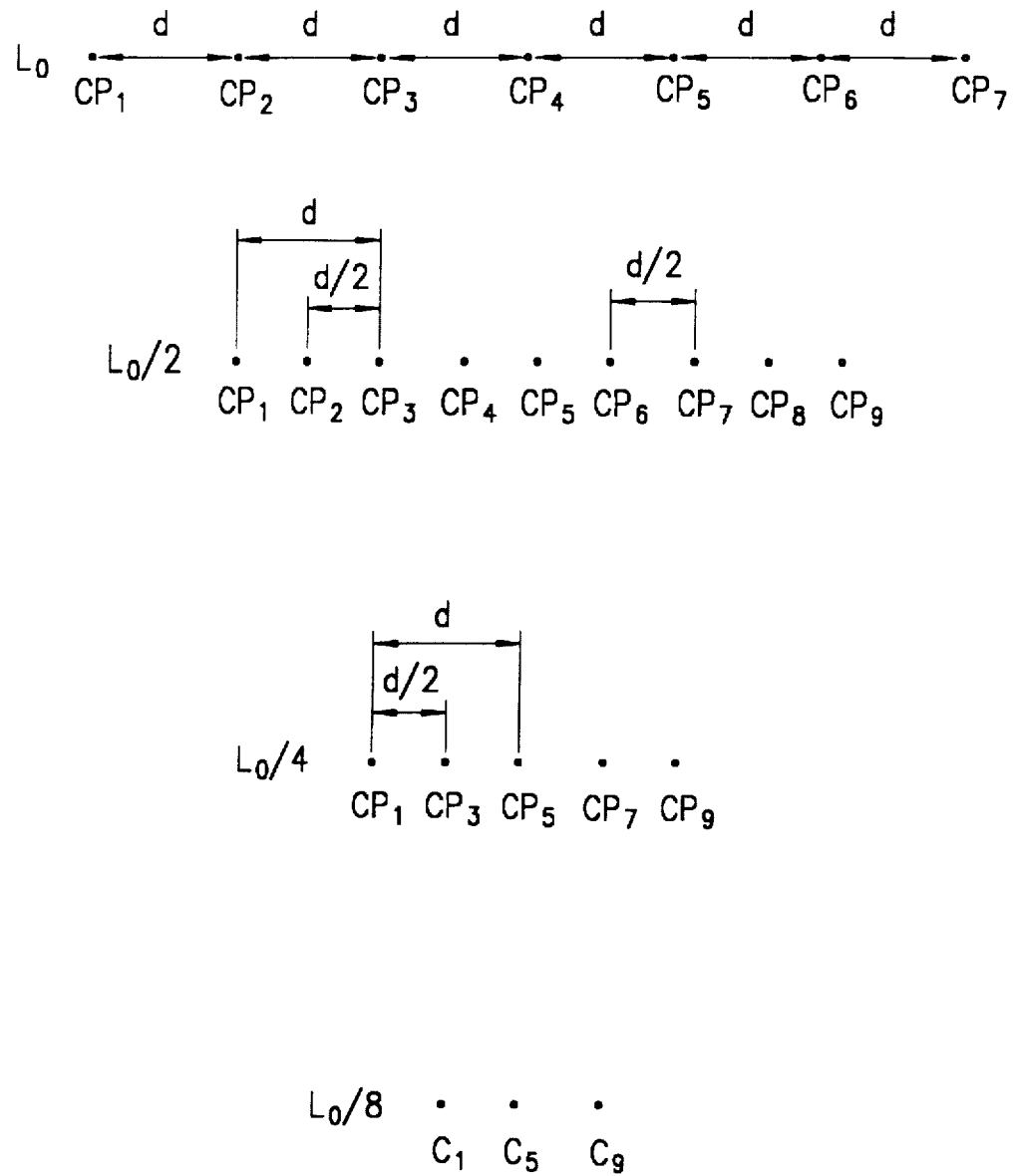
FIG. 6 is a schematic illustration of the method of the present invention for defining axial finish cut paths and determining which cut paths are to be terminated at different depths within the bone cavity.

Referring to FIGS. 5 and 6, assume that cross-sectional template $504_1$ is the top-most (i.e. adjacent the entrance end of the cavity) cross section in the cavity to be cut. This template will be defined to be at a zero depth ($L_0$) within the cavity. A plurality of points $CP_i$ will be defined along the line $506_1$, where these points will be the starting locations for the rotary cutter used to implement the finish cuts along the cavity wall. The number of points $CP_i$ needed will depend on the distance d between adjacent points necessary to maintain the radial cusp height therebetween below the maximum allowable value, typically in the range from 0.01 mm to 0.1 mm. This distance, or the number of points, can be defined in a variety of ways. Most simply, the distances d can be calculated by breaking the periphery of the cross-section template down into line segments and arc segments. Then for line segments, the distance d between finish cut path points $CP_i$ is calculated by the following formula:

| Formula 1 |
|---|
| $d = 2(2rc-c^2)^{0.5}$, where d = distance between $CP_1$ and $CP_{i+i}$ at $L_0$; r = radius of cutter; and c = maximum cusp height. |

For adjacent cutter path points $CP_i$ on an arc, the formula for determining distance is as follows:

| Formula 2 |
|---|
| $d = 2R \cos^{-1}(t_1^2 + t_2)/(2t_1 t_3)$ where d = distance between $CP_i$ and $CP_{i+i}$; R = radius of arc; r = radius of cutter; c = maximum cusp height; $t_1 = R - c$; $t_2 = R(R - 2r)$; and $t_3 = r - C$. |

As described thusfar, the method for initiating finish cutting is of a type which has been employed in the ROBODOC™ surgical system for some time. Such prior methodology, however, relies on translating the rotary cutter along axial finish cut paths each of which extends substantially the entire length of the cavity being cut. While this is an acceptable procedure since the axial cusps which remain between adjacent cut paths diminishes in the direction toward the terminal end 502, it is wasteful of time since the greater smoothness in the distal regions of the cavity is not a requirement. The present invention reduces the overall time required to achieve finish cutting of the bone cavity by limiting the lengths of as many of the cut paths as possible without exceeding the maximum radial cusp pipe requirement.

Referring now to FIG. 6, plurality of points $CP_i$ defining cutter paths at various depths within a bone cavity are shown schematically. In particular, the distances at the top of the cavity ($L_0$) are shown in a rolled-out configuration with equal distances d therebetween. It will be assumed that the distances d have been calculated to maintain the radial cusp heights between adjacent cut paths below an acceptable limit. As cut paths proceed down the cavity, however, the adjacent points $CP_i$ on each cut path will move circumferentially closer together. When the depth reaches the level where the peripheral distance about the cavity cross-section through that depth is equal to one-half the original length ($L_0/2$), then the adjacent points $CP_i$ have moved together so that the average distances d therebetween is equal to about half of the original distance d. This means that the cut paths on either side of any given cut paths (e.g. $CP_1$ and $CP_3$ on either side of $CP_2$) now lie within the distance d and that even if cut path $CP_2$ is terminated, the remaining adjacent cut paths ($CP_1$ and $CP_3$) are sufficiently close to assure that the cusp height therebetween will not exceed the maximum acceptable limit. Thus, when the cutting has reached a depth where the circumferential length about the cavity is equal to $L_0/2$ then each alternate cut path can be terminated. When the number of cut paths is even, it will be possible to reduce the number of cut paths in half. When the number is odd, the reduction may only be a number equal to one-half of the original number plus one. This is because it would not be acceptable to terminate two adjacent cut paths.

As the cavity continues to taper in the direction toward the terminal end 502, the circumferential length about the cavity will continue to be reduced. When the circumferential length reaches a value equal to $L_0/4$, it will be further possible to terminate alternate ones of the cut paths. Similarly, when the depth of the cavity reaches a point where the circumferential length has been reduced to $L_0/8$, then further alternate cut paths may be eliminated. Such sequential elimination may be continued until the terminal end 502 of the cavity is reached.

Thus, the information as to both positions of cut path and lengths of cut paths will be included in the cut files which are transferred from the pre-operative planning station to the robotic cutter system. This information will usually be incorporated into a tape, disk, or other tangible medium which is transferred between the systems. Moreover, the instructions for determining the cutter movement and positioning will be computed by the pre-operative planning station.

Figure 7:
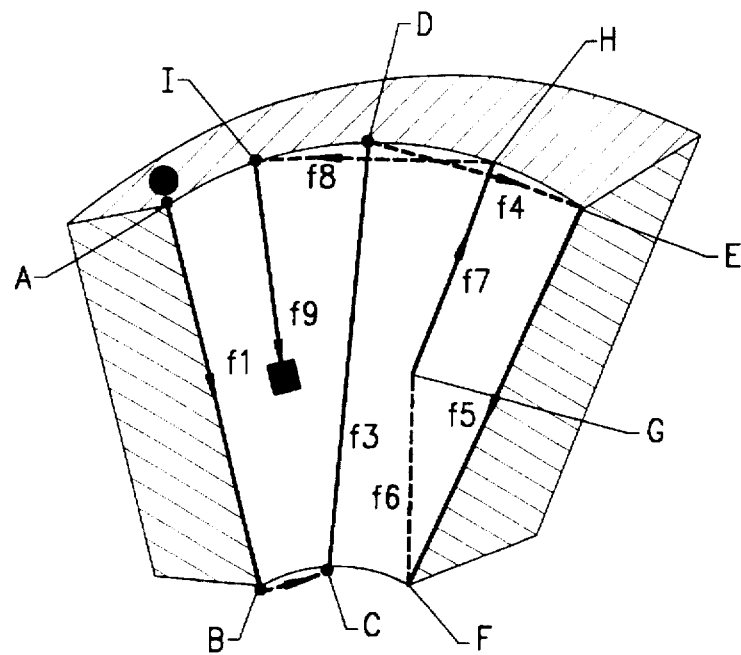
FIG. 7 illustrates an exemplary finish cut path map for a rotary cutter in a tapered cavity free from convexities.
Figure 8:
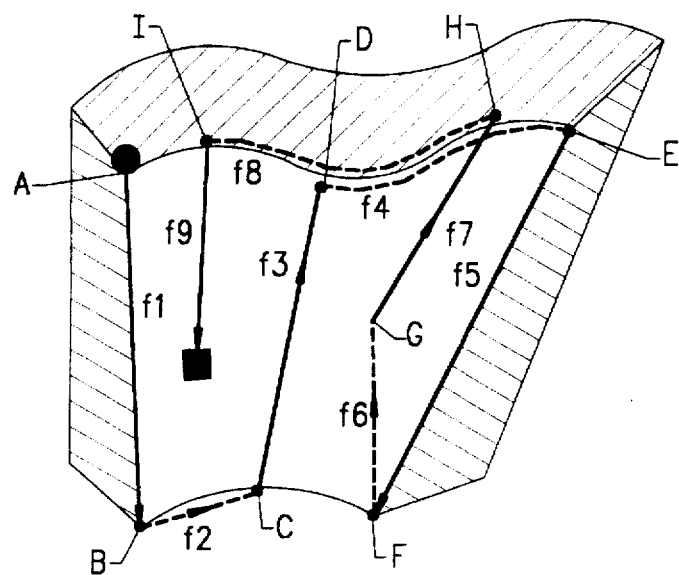
FIG. 8 illustrates an alternative exemplary cut path map for rotary cutter in a bone cavity having a convexity.

Referring now to FIGS. 7 and 8, optimum cutting according to the present invention further requires that the cutter head be moved in as efficient pattern as possible. The ability to move the cutter will depend, in part, whether the cavity being cut contains any convexities. When the cavity is free from convexities, as shown in FIG. 7, the cutter will typically move from a point A along a line $f_1$ to a point B near the terminal end 502 of the cavity. Then, the cutter will move laterally to a point C, also at the bottom of the cavity, and will then be moved upwardly along line $f_3$ to a point D at the top of the cavity. The cutter is then moved along a line $f_4$ to point E where it is moved fully to point F at the bottom of the cavity. At this point, it is necessary for the cutter to move (without cutting) to the bottom point G of a shortened cut path $f_7$ to point H at the top of the cavity. The cutter can then move along line $d_8$ to point I to make a final downward cut along line $f_9$ to a terminal point. This cutting pattern, of course, is extremely simplified, but is representative of the optimization of the cut paths according to the present invention. It should be noted that total translational motion of the robot arm is not substantially reduced by the method of the present invention. The cutting time, however, is substantially reduced. The robot arm may be moved much more rapidly through space when bone material is not being cut.

The cutting pattern as shown in FIG. 7 must be modified slightly when the bone cavity includes convexities, as shown in FIG. 8. In particular, note that the cutting paths are similar, except that the robot arm cannot always move through a straight line. For example, movements between points D and E must follow the peripheral contour of the cavity (since the convexity physically constructs a straight path between the points). Similarly the arm must follow a curved line between points H and I for the same reason.

Although the foregoing invention has been described in some detail by way of illustration and example, for purposes of clarity of understanding, it will be obvious that certain changes and modifications may be practiced within the scope of the appended claims.

What is claimed is:

1. An improved method for cutting a tapered cavity into an elongate bone, said cavity being of the type wherein an enlarged entrance tapers down in an axial direction and over an axial length to a small terminal end and said method being of the type wherein the bone is first rough cut to produce a rough cavity and then finish cut by translating a rotary cutter axially along a plurality of circumferentially spaced-apart finish cut paths to form axial grooves separated by axial cusps in a cavity wall which approximates a preplanned cavity model, wherein the improvement comprises selectively shortening the axial lengths of some but not all of the finish cut paths to a distance less than the axial cavity length whereby total cutting time is reduced.

2. An improved method as in claim 1, wherein the finish cut paths are equally spaced-apart at the cavity entrance and wherein the distances therebetween decrease uniformly toward the terminal end of the cavity, wherein the improvement further comprises terminating an axial finish path when the distance between the two immediately adjacent finish cut paths is equal to or less than the distance between a pair of adjacent finish cut paths at the entrance end of the cavity.

3. A method for cutting a tapered cavity into an elongate bone, said method comprising:

providing a cavity model defining a cavity envelope having dimensions including axial length from an entrance end to a terminal end thereof and cross-sectional geometries and dimensions at various depths from the entrance toward the terminal end;

rough cutting the cavity to remove bone material along the cavity axis to approximate the shape of the cavity envelope;

finish cutting the tapered cavity with a rotary cutter having a radius (r) as follows:

defining a plurality of finish cut paths which are spaced radially inward from the envelope by the distance r and which are circumferentially spaced-apart by a distance (d) selected to produce at the entrance end of the cavity a preselected radial cusp height between adjacent cuts, wherein said radial cusp height will diminish as the cavity tapers and the finish cut paths move circumferentially closer together; and finish cutting with the rotary cutter along each of the finish cut paths, wherein cutting along a particular cut path is terminated when the two cut paths adjacent to said particular cut path become sufficiently close so that the cusp height between said adjacent cut paths is equal to or less than the preselected radial cusp height and wherein cutting along said adjacent cut paths is continued.

4. A method as in claim 3, wherein the rough cutting step comprises penetrating a rotary cutter in an axial direction into the bone and advancing the cutter about the circumferential periphery of the envelope in a plurality of successive cross-sectional planes, wherein the cutter may touch but not cross the envelope.

5. A method as in claim 3, wherein the same rotary cutter is used for both rough cutting and finish cutting.

6. A method as in claim 4, wherein the rotary cutter is a disk cutter or a ball cutter.

7. A method as in claim 3, wherein the defining and finish cutting steps further comprise:

determining the number ($N_0$) of finish cut paths necessary to produce the predetermined cusp height when the cut paths are evenly distributed around the cavity circumference at the cavity entrance;

determining the circumferential length ($h_0$) about the cavity envelope at the entrance end;

determining the cavity depth ($d_1$) from the entrance end toward the terminal end at which the circumferential length ($L_1$) about the cavity has diminished to a value of $h_0/2$; and terminating alternate ones of the finish cut paths at depth $d_1$, except that if $N_0$ is odd two adjacent non-terminated cut paths will remain.

8. A method as in claim 7, further comprising:

determining the cavity depth ($d_2$) at which the circumferential length ($L_2$) has diminished to a value of $L_0/4$; and terminating alternate ones of the cut paths at depth $d_2$, except that the same two non-terminated cut paths will remain if $N_0$ is odd.

9. A method as in claim 8, further comprising:

determining the cavity depth ($d_3$) at which the circumferential length ($L_3$) has diminished to a value of $L_0/8$; and terminating alternate ones of the cut paths, except that the same two non-terminated cut paths will remain if $N_0$ is odd.

* * * * *